(12) United States Patent
Gattiker et al.

(45) Date of Patent: Jun. 5, 2018
(10) Patent No.: US 9,987,502 B1

(54) RADIATION THERAPY TREATMENT PLANNING USING REGRESSION

(71) Applicant: INTERNATIONAL BUSINESS MACHINES CORPORATION, Armonk, NY (US)

(72) Inventors: Anne E. Gattiker, Austin, TX (US); Sani R. Nassif, Austin, TX (US); Tom Osiecki, Austin, TX (US); Chin Ngai Sze, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/371,002

(22) Filed: Dec. 6, 2016

(51) Int. Cl.
*A61N 5/10* (2006.01)
*G06T 15/08* (2011.01)

(52) U.S. Cl.
CPC .......... *A61N 5/103* (2013.01); *A61N 5/1084* (2013.01); *G06T 15/08* (2013.01); *A61N 2005/1087* (2013.01); *G06T 2210/41* (2013.01)

(58) Field of Classification Search
CPC .. A61N 5/1031; A61B 2576/02; G06T 15/08; G06T 7/11
USPC .......... 345/424, 427; 378/65, 64; 250/492.2, 250/492.22, 492.3
See application file for complete search history.

(56) References Cited

U.S. PATENT DOCUMENTS

| | | | | |
|---|---|---|---|---|
| 5,544,283 A * | 8/1996 | Kaufman | ................ | G06T 15/06 345/424 |
| 5,760,781 A * | 6/1998 | Kaufman | ................ | G06T 1/20 345/424 |
| 6,411,675 B1 * | 6/2002 | Llacer | ................ | A61N 5/1031 378/64 |
| 8,315,357 B2 * | 11/2012 | Zhu | ................ | A61N 5/1031 378/65 |
| 8,644,571 B1 * | 2/2014 | Schulte | ................ | A61N 5/1039 250/307 |
| 8,986,186 B2 | 3/2015 | Zhang et al. | | |
| 9,387,344 B2 * | 7/2016 | Sgouros | ................ | A61N 5/1031 |

(Continued)

OTHER PUBLICATIONS

Bednarz, Ph.D., Bryan, "Monte Carlo Methods in Proton Therapy," Oct. 2005, Powerpoint Presentation (39 pages).

(Continued)

*Primary Examiner* — David A Vanore
(74) *Attorney, Agent, or Firm* — Tutunjian & Bitetto, P.C.; William J. Stock (57) ABSTRACT

A method and system are provided. The method includes splitting, by a processor based on radiation beamlet contributions to neighboring voxels, at least one row in a voxel-beamlet matrix and corresponding elements of a target dose vector prior to, and in preparation for, a regression operation. The voxel-beamlet matrix has a row for each of a plurality of voxels in a three-dimensional patient volume and a column for each of a plurality of radiation beamlets. The target dose vector represents a desired energy amount for each of the plurality of voxels in the three-dimensional patient volume. The target dose vector corresponds voxel-by-voxel to rows in the voxel-beamlet matrix. The method further includes performing, by the processor, the regression operation on the voxel-beamlet matrix and target dose vector to obtain beamlet weights. The method also includes determining an actual radiation dosing scheme for a given patient based on the beamlet weights.

20 Claims, 6 Drawing Sheets

(56) References Cited

U.S. PATENT DOCUMENTS

| | | | | |
|---|---|---|---|---|
| 2004/0122709 | A1* | 6/2004 | Avinash | G06F 19/322 705/2 |
| 2004/0122787 | A1* | 6/2004 | Avinash | G06F 19/345 706/50 |
| 2005/0010106 | A1* | 1/2005 | Lang | A61B 6/469 600/425 |
| 2009/0234626 | A1* | 9/2009 | Yu | A61N 5/1031 703/11 |
| 2013/0030762 | A1* | 1/2013 | Mercier | A61N 5/1031 702/179 |
| 2015/0348259 | A1* | 12/2015 | Souza | G06T 7/11 382/131 |

OTHER PUBLICATIONS

Paganetti, Harald et al., "Proton Beam Radiotherapy—The State of the Art," New Technologies in Radiation Oncology (Medical Radiology Series), Oct. 2005, pp. 1-36, Massachusetts General Hospital, Boston, MA, USA.

Li, Yupeng et al., "An efficient dose calculation strategy for intensity modulated proton therapy," Physics in Medicine and Biology, Jan. 2011, pp. N71-N84, Phys. Med. Biol. 56 (2011), 2011 Institute of Physics and Engineering in Medicine.

Ericsson, Malin, "Intensity Modulated Proton Therapy (IMPT)—A comparative treatment planning study," Master of Science Thesis, Jan. 2007, pp. 1-76, Department of Radiation Physics, Lund University Hospital, Medical Radiation Physics Clinical Sciences, Lund, Lund University.

Breedveld, Sebastiaan et al., "A novel approach to multi-criteria inverse planning for IMRT," Physics in Medicine and Biology, Oct. 2007, pp. 6339-6353, Phys. Med. Biol. 52 (2007), 2007 IOP Publishing Ltd.

Gonzalo, Cabal et al., "Target Definition and Treatment Planning in Particle Therapy using Monte Carlo Error Propagation Analysis," Powerpoint Presentation, 1st New Mexico Workshop on Monte Carlo for Particle Therapy Treatment Planning Albuquerque, New Mexico May 16-18, 2011 (45 pages).

Chen, Wei et al., "A fast optimization algorithm for multicriteria intensity modulated proton therapy planning," American Association of Physicists in Medicine, Aug. 2010, pp. 4938-4945, Med. Phys. 37 (9).

Chvetsov, Alexei V. et al., "Regularization of inverse planning for intensity-modulated radiotherapy," American Association of Physicists in Medicine, Jan. 2005, pp. 501-514, Med. Phys. 32 (2).

Gui, Vi et al., "Constrained Grouped Sparsity," Conference Paper, Dec. 2012, pp. 1-27, Proceedings of the 25th Australasian joint conference on Advances in Artifcial Intelligence.

Fredricksson, Albin, "Automated Improvement of Radiation Therapy Treatment Plans by Optimization Under Reference Dose Constraints," Physics in Medicine and Biology 57, Nov. 2012, pp. 7799-7811.

Friedman, Jerome et al., "A note on the group lasso and a sparse group lasso," arXiv preprint arXiv, Jan. 2010, pp. 1-8, 1001.0736.

Holdsworth, Clay et al., "The use of a multiobjective evolutionary algorithm to increase flexibility in the search for better IMRT plans," American Association of Physicists in Medicine, Apr. 2012, pp. 2261-2274, Med. Phys. 39 (4).

Petit, Steven et al., "Increasing maximum tumor dose to manage range uncertainties in IMPT treatment planning," Physics in Medicine and Biology, Sep. 2013, pp. 7329-7341, Phys. Med. Biol. 58 (2013), 2013 Institute of Physics and Engineering in Medicine.

Lim, Gino J. et al., "A two-phase method for selecting IMRT treatment beam angles: Branch-and-Prune and local neighborhood search," European Journal of Operational Research, Feb. 2012, pp. 609-618, 217 (3).

Lim, Gino J. et al., "Iterative Solution Methods for Beam Angle and Fluence Map Optimization in Intensity Modulated Radiation Therapy Planning," OR Spectrum, Apr. 2008, pp. 289-309, 30 (2).

Unkelbach, Jan et al., "The dependence of optimal fractionation schemes on the spatial dose distribution," Physics in medicine and biology, Dec. 2012, pp. 1-14, 58(1) 159.

Chen, Wei et al., "Including Robustness in Multi-criteria Optimization for Intensity Modulated Proton Therapy," Department of Radiation Oncology, Massachusetts General Hospital and Harvard Medical School, Dec. 2011, pp. 1-17, arXiv 1112.5362 v1.

Craft, David L. et al., "Approximating convex Pareto surfaces in multiobjective radiotherapy planning," American Association of Physicists in Medicine, Aug. 2006, pp. 3399-3407, Med. Phys. 33 (9).

Fredriksson, Albin et al., "Minimax optimization for handling range and setup uncertainties in proton therapy," American Association of Physicists in Medicine, Mar. 2011, pp. 1672-1684, Med. Phys. 38 (3).

Paganetti, Harald, "Range uncertainties in proton therapy and the role of Monte Carlo simulations," Phys Med Biol. Jun. 2012, pp. 1-27, 57 (11).

Cao, Wenhua et al., "Beam angle selection in Intensity Modulated Proton Therapy treatment planning for prostate cancer," Proceedings of the 2011 Industrial Engineering Research Conference, Jan. 2011, pp. 2-8.

Siebers, PH.D, Jeffrey V. et al., "Monte Carlo Applications in IMRT Planning and Quality Assurance," Proceedings of the 2006 AAPM Summer School, edited by I. Chetty (Medical Physics Publishing Corp, Madison, WI, 2006), Jun. 2006, pp. 1-33.

Iordache, Marian-Daniel et al., "Hyperpectral Unmixing with Sparse Group Lasso," Geoscience and Remote Sensing Symposium (IGARSS), Oct. 2011, pp. 3586-3589, 2011 IEEE International.

Kim, Taeho et al., "Inverse planning for IMRT with nonuniform beam profiles using total-variation regularization (TVR)," American Association of Physicists in Medicine, Dec. 2010, pp. 57-66, Med. Phys. 38 (1).

Zhu, Lei et al., "Using total-variation regularization for intensity modulated radiation therapy inverse planning with field-specific numbers of segments," Phys. Med. Biol., Nov. 2008, pp. 6653-6672, 53 (2008).

Tibshirani, Robert, "Regression shrinkage and selection via the lasso: a retrospective," Journal of the Royal Statistical Society, Sep. 2011, pp. 273-282, B (2011) 73, Part 3.

Simon, Noah et al., "Standardization and the Group Lasso Penalty," Statistica Sinica, Jul. 2012, pp. 1-21.

Unkelbach, Jan et al., "Reducing the sensitivity of IMPT treatment plans to setup errors and range uncertainties via probabilistic treatment planning," American Association of Physicists in Medicine, Dec. 2008, pp. 149-164, Med. Phys. 36 (1).

Xia, Ph. D, Ping, "Inverse Planning Techniques for IMRT," Powerpoint Presentation, Jul. 2004, (22 pages).

Liu, Wei et al., "Effectiveness of robust optimization in intensity-modulated proton therapy planning for head and neck cancers," American Association of Physicists in Medicine, Apr. 2013, pp. 051711-1-051711-9, Med. Phys. 40 (5).

Cao, Wenhua et al., "Proton energy optimization and reduction for intensity-modulated proton therapy," Phys Med Biol., Nov. 2014, pp. 6341-6354, 59 (21).

Cao, Wenhua et al., "Incorporating deliverable monitor unit constraints into spot intensity optimization in intensity modulated proton therapy treatment planning," Phys Med Biol., Aug. 2013, pp. 5113-5125, 58 (15).

Liu, Wei et al., "Robust optimization of intensity modulated proton therapy," American Association of Physicists in Medicine, Feb. 2012, pp. 1079-1092, Med. Phys. 39 (2).

Yuan, Ming et al., "Model selection and estimation in regression with grouped variables," J. R. Statist., Nov. 2006, pp. 49-67, Soc. B (2006) 68, Part 1.

\* cited by examiner

RADIATION THERAPY TREATMENT PLANNING USING REGRESSION

BACKGROUND

Technical Field

The present invention relates generally to radiation therapy and, in particular, to radiation therapy treatment planning using regression.

Description of the Related Art

Proton (or other heavier ions such as carbon) Beam Radiation Therapy Treatment for cancer aims to shoot protons from a source into the body in such a way that the protons deposit a large amount of energy into the tumor, while minimizing the amount of energy deposited into healthy tissue. The tumor is referred to as the target volume, using terms such as clinical target volume (CTV), scanning target volume (STV), and planning target volume (PTV), while parts of the healthy tissue to be avoided are termed Organs at Risk, or OARs. Treatment planning involves choosing the energies of the proton beams that are shot, as well as the angles from which they are shot and calculating the optimal duration at a given current for each energy-angle pair. Assuming pencil beam therapy, the time for each beamlet in a scan matrix of beamlets is determined. Planning is usually done using the outputs of a particle simulator that indicates where in the patient's body candidate protons of different energies and shot from different angles drop their energy. A solution to the treatment planning problem determines, using those outputs and a knowledge of the target energies desired in each body region, how much energy and from which angles to shoot protons as well as for how long at a given current. Typically, that problem is solved using Linear Programming (LP) or Quadratic Programming (QP) or other optimization approaches, but typical solutions can be slow, have limitations in terms of problem formulation, and may not provide accurate or efficient enough solutions.

SUMMARY

According to an aspect of the present principles, a method is provided. The method includes splitting, by a processor based on radiation beamlet contributions to neighboring voxels, at least one row in a voxel-beamlet matrix and corresponding elements of a target dose vector prior to, and in preparation for, a regression operation. The voxel-beamlet matrix has a row for each of a plurality of voxels in a three-dimensional patient volume and a column for each of a plurality of radiation beamlets. The target dose vector represents a desired energy amount for each of the plurality of voxels in the three-dimensional patient volume. The target dose vector corresponds voxel-by-voxel to rows in the voxel-beamlet matrix. The method further includes performing, by the processor, the regression operation on the voxel-beamlet matrix and target dose vector to obtain beamlet weights. The method also includes determining an actual radiation dosing scheme for a given patient based on the beamlet weights.

According to another aspect of the present principles, a system is provided. The system includes a memory device and a processor. The processor is configured to split, based on radiation beamlet contributions to neighboring voxels, at least one row in a voxel-beamlet matrix and corresponding elements of a target dose vector prior to, and in preparation for, a regression operation. The voxel-beamlet matrix has a row for each of a plurality of voxels in a three-dimensional patient volume and a column for each of a plurality of radiation beamlets. The target dose vector represents a desired energy amount for each of the plurality of voxels in the three-dimensional patient volume. The target dose vector corresponds voxel-by-voxel to rows in the voxel-beamlet matrix. The processor is further configured to perform the regression process on the voxel-beamlet matrix and target dose vector to obtain beamlet weights. The processor is also configured to determine an actual radiation dosing scheme for a given patient based on the beamlet weights.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles are directed to radiation therapy treatment planning using regression. While one or more embodiments of the present principles may be described with respect to proton radiation therapy, the present principles can be applied to any particle beam cancer therapy.

In an embodiment, the present principles pose radiation treatment planning as a regression problem. In an embodiment, a novel regression formulation in accordance with present principles (hereinafter "regression formulation") is used as an alternative to typical Linear Programming (LP), Quadratic Programming (QP) or other optimization formulations. Advantageously, the described regression formulation can provide improvements in terms of speed, problem formulation and accuracy.

Typically, the outputs of a particle simulation are captured in a voxel-beamlet matrix referred to herein as "vbmat" in short. The vbmat has a row for each voxel in a three-dimensional (3-D) patient volume and a column for each beamlet. A beamlet is a stream of protons of a given energy shot from a given angle at a given location in the scan matrix. Cells (entries) of the vbmat give the energy deposited in the row's voxel when the column's beamlet is applied for a known duration and current. Each voxel is identified as belonging to a given body region, e.g., the target volume (aka STV) or an Organ At Risk (aka OAR). Targets are set based on the amount of energy desired to be deposited in a given body region. For the STV, targets are usually lower bounds, whereas for OARs targets are typically upper bounds.

A target vector is created that expresses a desired energy for each voxel in the 3-D patient volume. Rows in the vbmat correspond voxel-by-voxel to elements in the target vector. A problem to be solved, to which an embodiment of the present principles is applied, can be cast as vbmat*vector-of-beamlet-weights=target vector+error, where vbmat and the target vector are known, the vector-of-beamlet weights is unknown (and solved for) and the error is desired to be small. Residuals are the differences between the "predicted" values (vbmat*vector-of-beamlet-weights) and the target vector. The vector-of-beamlet-weights can be solved for, for example by finding the vector-of-beamlet-weights that minimizes an error function of the residuals, e.g., a sum of squared residuals or a sum of absolute values of residuals or using other functions. The regression can be a weighted regression in which case rows of vbmat and corresponding elements of the target vector are multiplied by a weighting factor that affects how much influence the corresponding voxel has on the solved-for vector-of-beamlet-weights.

Regression is used to solve for the vector-of-beamlet-weights, given a known vbmat and target vector. The vector-of-beamlet-weights is the solution to the treatment planning problem in that it determines how long each beamlet should be turned on at a given current during treatment.

Figure 1:
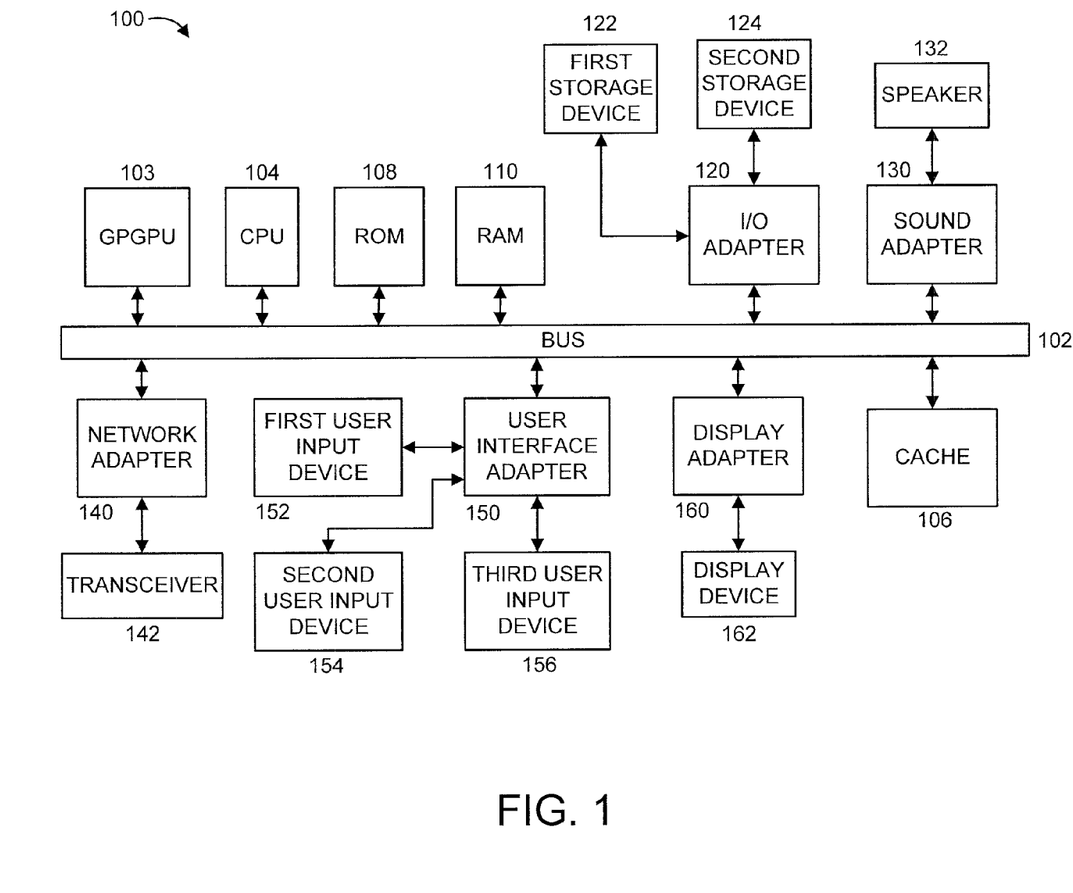
FIG. 1 shows an exemplary processing system 100 to which the present principles may be applied, in accordance with an embodiment of the present principles.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
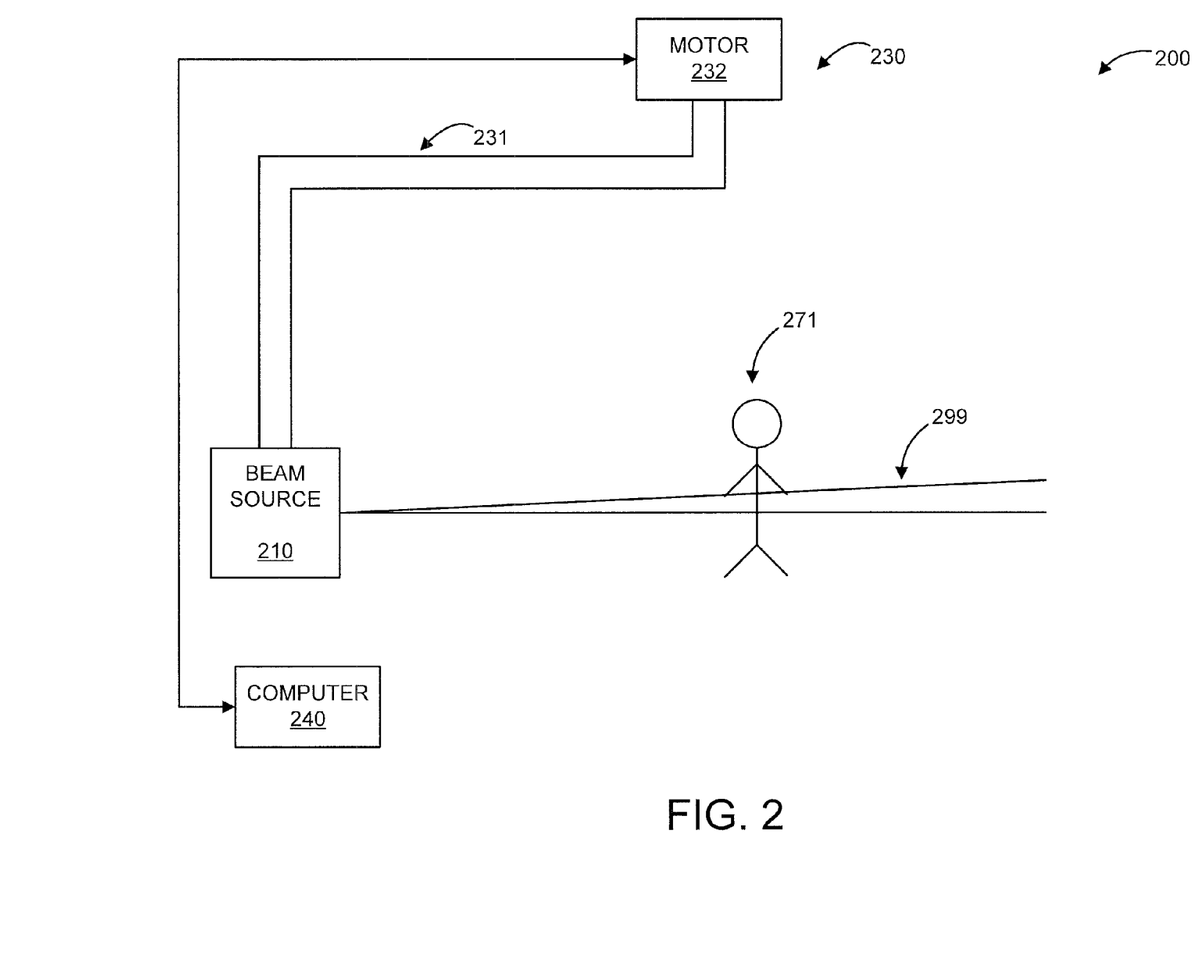
FIG. 2 shows an exemplary radiation therapy system 200 to which the present principles can be applied, in accordance with an embodiment of the present principles.
Figure 3:
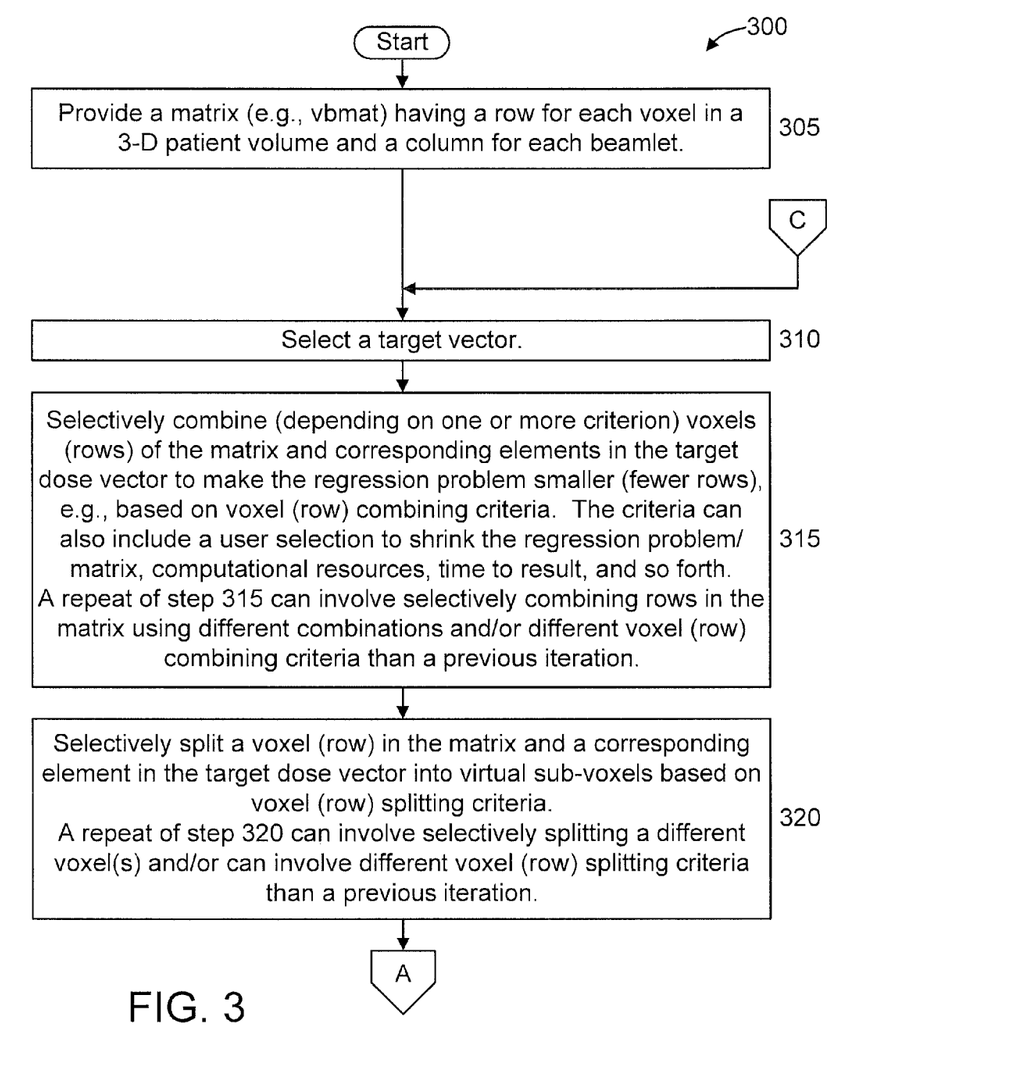
FIGS. 3-6 show an exemplary method 300 for proton radiation therapy treatment plan optimization using regression, in accordance with an embodiment of the present principles.
Figure 4:
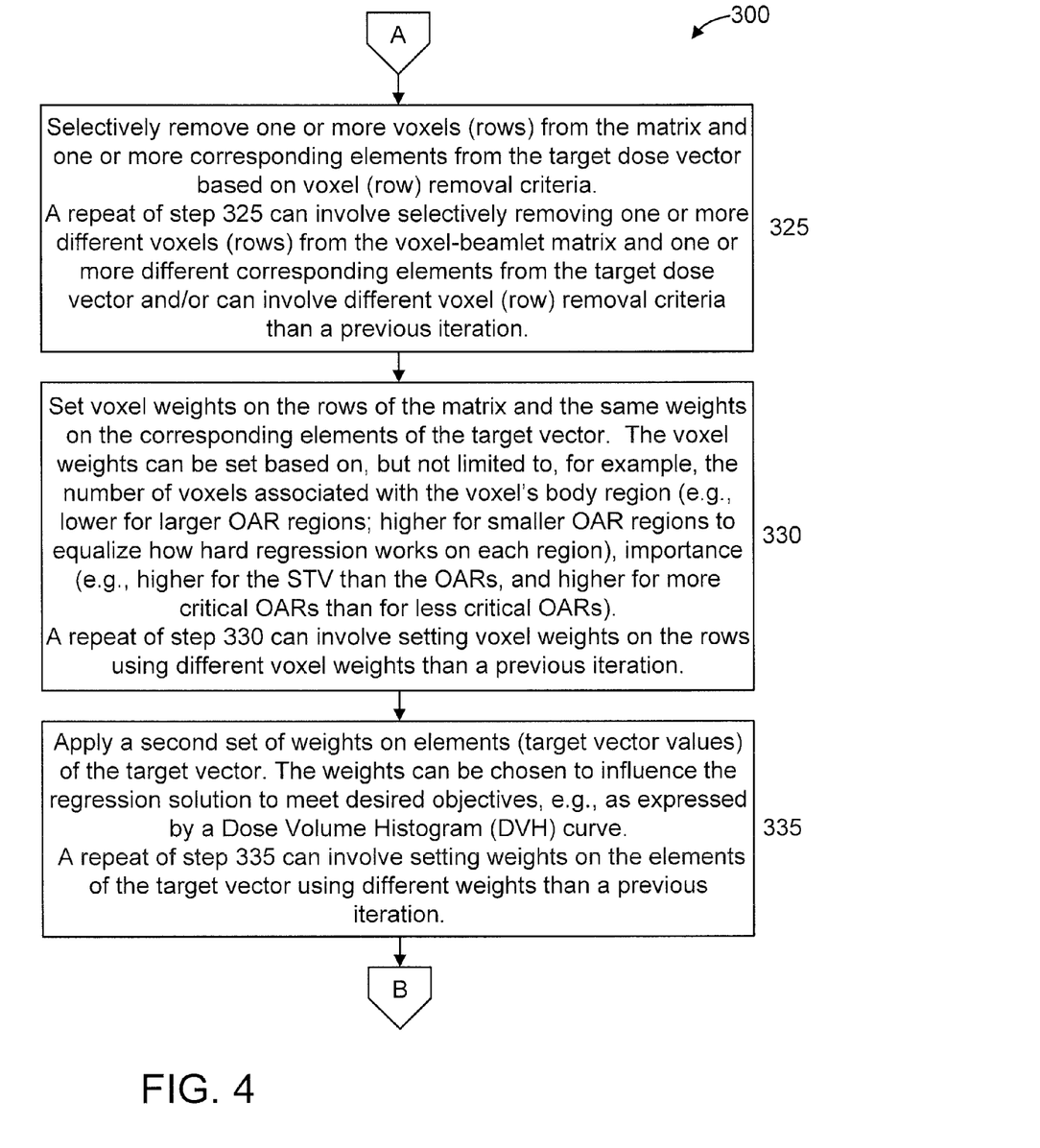
Figure 5:
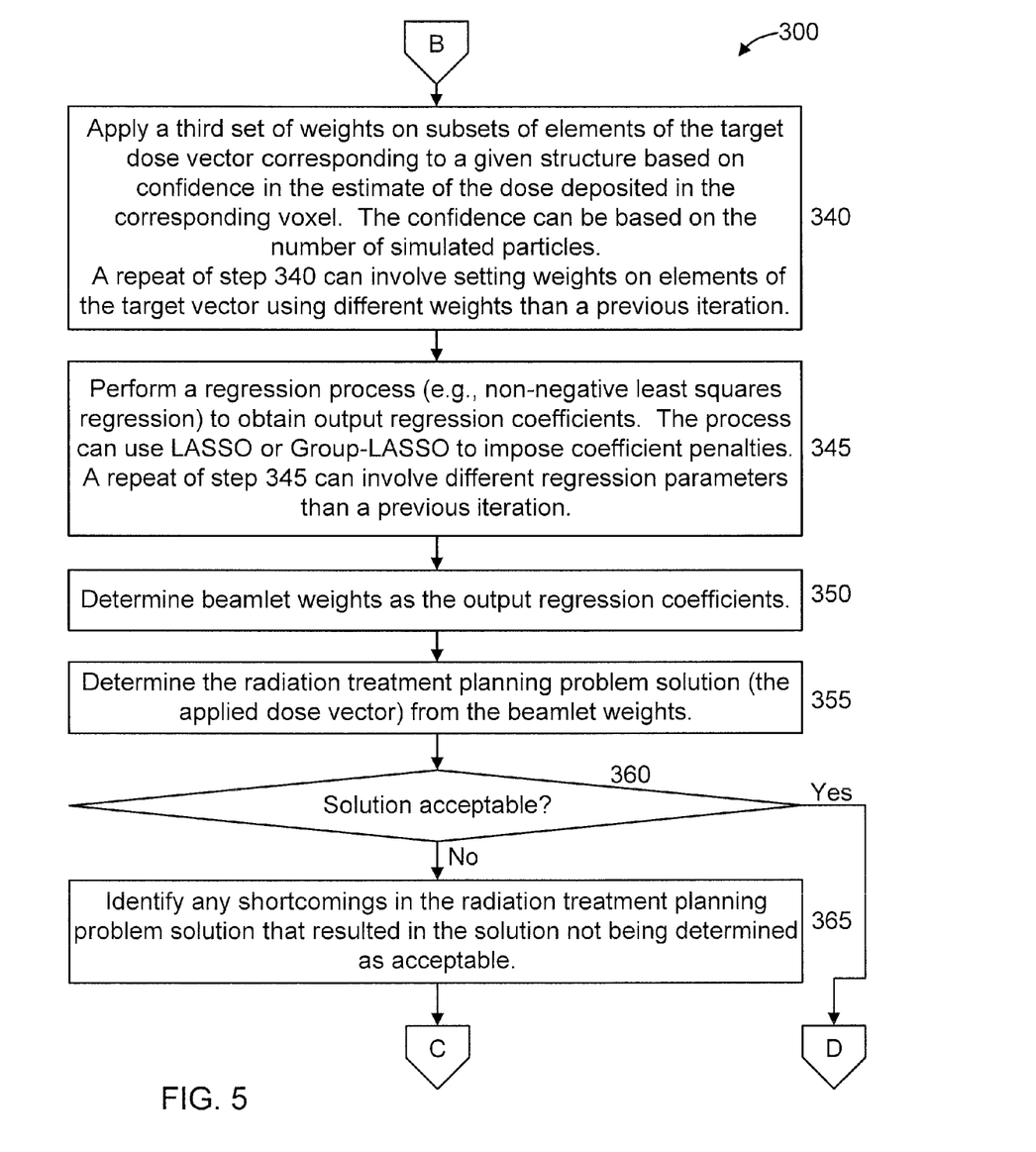
Figure 6:
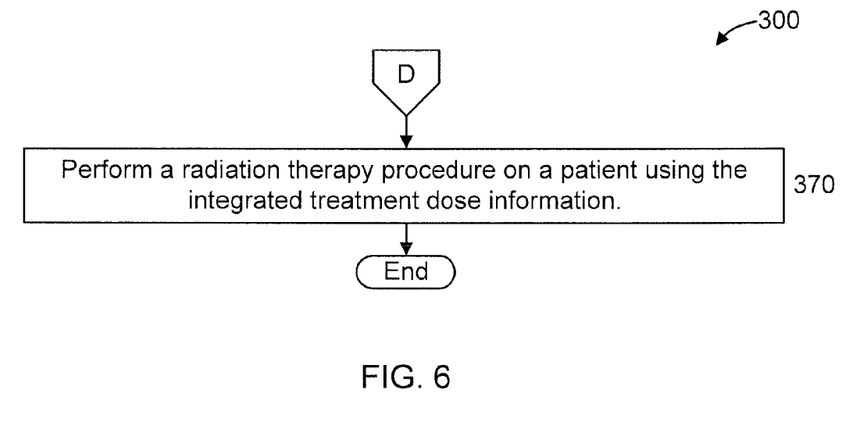

Moreover, it is to be appreciated that system 200 described below with respect to FIG. 2 is a system for implementing respective embodiments of the present principles. Part or all of processing system 100 may be implemented in one or more of the elements of system 200.

Further, it is to be appreciated that processing system 100 may perform at least part of the method described herein including, for example, at least part of method 300 of FIGS. 3-6. Similarly, part or all of system 200 may be used to perform at least part of method 300 of FIGS. 3-6.

FIG. 2 shows an exemplary radiation therapy system 200 to which the present principles can be applied, in accordance with an embodiment of the present principles.

The radiation therapy system 200 includes a beam source 210, a positional device 230, and a computer 240.

The beam source 210 provides a radiation source for emitting radiation 299 to a target structure. In an embodiment, the beam source 210 can include a particle accelerator. In an embodiment, the beam source generates beamlets. Assuming proton pencil beam therapy, a beamlet is a stream of protons of a given energy shot from a given angle at a given location in a scan matrix.

The positional device 230 is attached to and positions the beam source 210 relative to an object of interest (person) 271 to emit radiation to one or more target structures (e.g., cancer tumors) in the object of interest. Often, the positional device 230 includes a structural member 231 to secure the beam source 210 for positioning, and a motor 232 to position the structural member 231 with respect to the one or more target structures.

The computer 240 controls the elements of system 200. For example, the computer 240 activates the beam source 210, and controls the movement of the positional device 230. Wiring for such control can be within the structural member 231 or in some other arrangement. The computer 240 includes a processor 240A and a memory 240B. The processor 240A initiates the controlling of the other elements including, for example, the emission of radiation by the beam source 210. The memory 240B stores software for performing a radiation therapy process. The memory 240B can also store data generated during a radiation therapy process.

It is to be appreciated that the present principles are not dependent upon any particular type of radiation therapy system and, thus, can be used with any type of radiation therapy system, while maintaining the spirit of the present principles. Thus, it is to be further appreciated that system 200 is generally described and can include other elements and other capabilities, as readily recognized by one of ordinary skill in the art. Moreover, while system 200 is described in one embodiment as involving protons, systems employing other types of radioactive elements can also be used in accordance with the teachings of the present principles, while maintaining the spirit of the present principles. These and other variations of system 200, as well as other radiation therapy systems to which the present principles can be applied, are readily determined by one of ordinary skill given the teachings of the present principles provided herein, while maintaining the spirit of the present principles.

FIGS. 3-6 show an exemplary method 300 for proton radiation therapy treatment plan optimization using regression, in accordance with an embodiment of the present principles.

At step 305, provide a matrix having a row for each voxel in a 3-D patient volume and a column for each beamlet. In an embodiment, the matrix is a vbmat.

At step 310, select a target vector. A target vector expresses a desired dose for each voxel in the 3-D patient volume, based on a set of clinical protocols. The target vector is selected in such a way that the solution to the problem achieves clinical goals. For example, if the minimum dose required in each voxel of the STV is x, set the corresponding target vector elements to x+alpha1*x, where alpha1 is a fraction less than one. Similarly if the maximum dose allowed in each voxel of an OAR is y, set the corresponding target vector elements to y−alpha2*y, where alpha2 is a fraction less than one.

At step 315, selectively combine (depending on one or more criterion) voxels (rows) of the matrix and corresponding elements in the target dose vector to make the regression problem smaller (fewer rows), e.g., based on voxel (row) combining criteria. The voxel combining criteria can include correlations in the matrix. The correlations can be based on, for example, the spatial relationship with other voxels in the same structure, where a structure is, for example, the STV or an OAR. They can also be mathematical correlations independent of spatial proximity. It is to be appreciated that it is not desirable to combine rows corresponding to different structures because the different structures would have different target values. The criteria used to perform the selective combining can also include a user selection to shrink the regression problem/matrix, computational resources, time to result, and so forth.

In an embodiment (where step 315 has already been performed at least once), a repeat of step 315 can involve selectively combining rows in the matrix using different combinations and/or voxel (row) combining criteria than a previous iteration.

Further regarding step 315, we note that physically-proximate voxels are likely to be similarly affected by beamlets. One can, for example, combine a set of eight neighboring voxels in a two-by-two-by-two cube into a single super-voxel. The rows corresponding to the eight original voxels would be summed, both in the vbmat and the target vector. Mathematical correlation between the vbmat rows corresponding to voxels can be another basis for combination. Combining rows can decrease collinearity in the vbmat and make the problem smaller.

At Step 320, selectively split a voxel (row) in the voxel-beamlet matrix and a corresponding element in the target dose vector into virtual sub-voxels based on voxel (row) splitting criteria. Row splitting criteria can be based on, for example, but is not limited to, the location of a voxel (to be split) relative to other voxels, e.g., an OAR voxel that neighbors an STV may be split such that the area of the original voxel closest to the STV is in a different sub-voxel from another area of the original voxel farther from the STV. Row splitting criteria can also be based on results of a previous iteration, e.g., a voxel with high residuals on the rows corresponding to it in a previous iteration may be split, possibly guided in part additionally by physical location of the voxel relative to other voxels.

Further regarding step 320, a method for splitting is explained by example in a two-dimensional case. Presume we wish to split a voxel into four equal-sized square sub-voxels. For each beamlet, the total dose in the subvoxels needs to be the same as the dose in the original voxel, $D_b$. Consider four neighbor voxels of the original voxel (above, below, left right). Given a given beamlet, find the dose deposited by the beamlet in each of the four neighboring voxels, $D_{b\text{-}above}$, $D_{b\text{-}below}$, $D_{b\text{-}left}$, $D_{b\text{-}right}$. Each subvoxel is assigned a portion of $D_b$ proportional to the dose deposited by the beamlet in each of its two closest neighbors. For example, the lower-left subvoxel's dose is $D_b*0.5*(D_{b\text{-}left}+D_{b\text{-}below})/(D_{b\text{-}left}+D_{b\text{-}below}+D_{b\text{-}right}+D_{b\text{-}above})$. The dose in the corresponding target dose vector elements can be split among the subvoxels in the same proportions or in such a way that the target doses influence the regression solution to meet desired objectives (similar to step 335), or in another way. Note step 335 can be used to redistribute the target dose among sub-voxels or change it for any sub-voxel. In a three-dimensional case, the voxels may be split into other shapes such as pyramids and there would be a greater number of neighbors. Moreover, the subvoxels do not need to be all the same size.

In an embodiment (where step 320 has already been performed at least once), a repeat of step 320 can involve selectively splitting a different voxel(s) and/or can involve different voxel (row) splitting criteria than a previous iteration.

At Step 325, selectively remove one or more voxels (rows) from the voxel-beamlet matrix and one or more corresponding elements from the target dose vector based on voxel (row) removal criteria.

Further regarding step 325, a voxel may be removed when a prior radiation treatment planning solution shows a high dose in an OAR structure or when a prior radiation treatment planning solution shows a large positive residual on a row corresponding to the voxel in an OAR structure. This may indicate, for example, that the structure borders the STV and some voxels within it will be very difficult to miss while simultaneously hitting the target, or that some voxels within the OAR are difficult to avoid for another reason. Based on the reasoning, for example, that once a cell is dead, it is dead, the amount a maximum criteria is exceeded does not matter. Taking the voxel out of the regression will prevent that voxel influencing the beamlet weights and will make the problem smaller. It is to be appreciated that a voxel can be split into subvoxels (per step 320) and then one of the subvoxels can be removed (per step 325).

In an embodiment (where step 325 has already been performed at least once), a repeat of step 325 can involve selectively removing one or more different voxels (rows) from the voxel-beamlet matrix and one or more different corresponding elements from the target dose vector and/or can involve different voxel (row) removal criteria than a previous iteration.

At step 330, set voxel weights on the rows of the matrix and the same weights on the corresponding elements of the target vector. In an embodiment, the voxel weights make the regression work harder (with increasing weight) or easier (with decreasing weight) on the voxel associated with the row. In other words, the voxel weights affect how much influence the voxel associated with the row has on the regression results. Higher weight means more influence. The voxel weights can be set based on, but not limited to, for example, importance (e.g., higher for the STV than the OARs, and higher for more critical OARs than for less critical OARs) or based on the sum of residuals of a voxel or group of voxels relative to the sum of the residuals of other voxels in a previous iteration.

In an embodiment (where step 330 has already been performed at least once), a repeat of step 330 can involve setting voxel weights on the rows using different weights than a previous iteration.

At step 335, apply a second set of weights on elements (target vector values) of the target vector. As noted above, a target vector expresses a desired dose for each voxel in the 3-D patient volume, based on a set of clinical protocols. For example, elements corresponding to SVT voxels may be set to a per-voxel minimum desired dosage, while elements corresponding to OAR voxels may be set to a value derived from a maximum allowable dosage. In an embodiment, step 335 includes applying weights to the target vector values to affect the regression results. For example, a weight of less than one can be set on target vector elements corresponding to voxels in one of the OARs to encourage a solution with less dose in the OAR compared with a solution without that weight applied. Similarly, a weight of less than one can be set on target vector elements corresponding to a subset of voxels in one of the OARs to encourage a solution with less dose in the subset of voxels compared with a solution without that weight applied. As another example, a weight of less than the weight applied in a previous iteration on a target vector element corresponding to a voxel can be applied to encourage a solution with less dose in the voxel than on the previous iteration.

In an embodiment (where step 335 has already been performed at least once), a repeat of step 335 can involve setting weights on the elements of the target vector using different weights than a previous iteration.

It is to be appreciated that the present principles involve both a target vector and a resulting dose vector. A target vector is chosen in such a way that the solution to the problem achieves clinical goals. A resulting dose vector is calculated based on the computed solution as resulting dose vector=vbmat*regression-derived beamlet weights.

It is to be appreciated that at this point, the resulting dose vector is incomplete, as the beamlet weights are not known yet (until step 345). As used herein, the term "resulting dose vector" refers to the vector that is obtained by multiplying vbmat times the regression-derived beamlet weights. The regression tries to make the resulting dose vector as close as possible to the target vector, but they will not be the same. The residual corresponding to each row of vbmat is the resulting dose vector element corresponding to the row minus the target vector element corresponding to the row.

At step 340, apply a third set of weights on subsets of elements of the target dose vector corresponding to a given structure based on confidence in the estimate of the dose deposited in the corresponding voxel. That confidence is an aggregate of the confidences in the dose estimates that comprise the rows of the vbmat corresponding to the voxel. The confidences can be a function of the number of particles in the particle simulations whose outputs are used to create vbmat. Further details of that potential dependence are described below. The aggregate can be, for example, proportional to the total number of simulated particles that deposit energy above a threshold in the voxel.

Further regarding step 340, target weights can be set more aggressively (e.g., higher for STV, lower for OAR) or less aggressively on the basis of the confidence of the estimate of the corresponding voxel's dose.

The vbmat includes estimates of dose per voxel per beamlet, where the estimates are typically based upon proton beam simulation. The number of protons in a beamlet's simulation that pass through a voxel can affect the confidence on the dose estimate for the beamlet for the voxel. For example, more protons leads to more confidence. Scattering generally results in more protons following a straight path than deflected paths, which in turn leads to fewer of the beamlet's simulation particles passing through some voxels that the beamlet passes through than others that it passes through. A lower confidence means there is a greater chance the actual dosage is different from the simulation result. Since one needs to ensure meeting the target for the STV while it is acceptable to exceed the target, setting a higher target weight for low-confidence voxels in the STV compensates for the chance the dosage is lower than the estimate. Similarly, setting a lower target weight for low-confidence voxels in the OAR compensates for the chance the dosage is higher than the estimate. Higher-confidence voxels in each region can be set less aggressively.

In an embodiment (where step 340 has already been performed at least once), a repeat of step 340 can involve setting weights on the elements of the target vector using different weights than a previous iteration.

At step 345, perform a regression process to obtain output regression coefficients. The regression acts on the modified vbmat, i.e., with rows combined, split, removed and/or weighted in steps in steps 315, 320, 325 and 330, respectively, and on the modified target vector, i.e., with elements combined, split and/or removed in steps in steps 315, 320 and 325, respectively and/or weighted in steps 330, 335 and 340. In an embodiment, a requirement of regression applied to the radiation treatment planning problem is that the solution is physically feasible using a real proton therapy system. To achieve a physically meaningful solution, we constrain the output coefficients to non-negative values. We also specify a zero intercept term. In an embodiment, we use non-negative least squares regression with no intercept term to achieve this goal. Other solution methods that put positivity constraints on the regression coefficients can also be used in accordance with the teachings of the present principles, while maintaining the spirit of the present principles. For example, the R function penalized can be used with L1 and L2 tuning factors set to zero, specification of no intercept term, no standardizing of covariates, model set to linear, and the non-negative coefficient constraint parameter set to true. The regression coefficients provide the beamlet weights which, in turn, provide the radiation treatment planning problem solution.

In an embodiment (where step 345 has already been performed at least once), a repeat of step 345 can involve different regression parameters than a previous iteration.

At step 350, determine beamlet weights as the output regression coefficients. In an embodiment, the beamlet weights are set equal to the output regression coefficients.

At step 355, determine the radiation treatment planning problem solution (the applied dose vector) from the beamlet weights. In an embodiment, the radiation treatment planning problem solution is determined using the following equation:

$$vbmat*\text{vector-of-beamlet-weights}=\text{applied dose vector}.$$

The beamlet weights indicate, e.g., the duration at a given current of proton beams of a given energy shot from a given angle at a given location in a scan matrix, with respect to a patient under treatment. It is to be noted that either the vector-of-beamlet-weights or the applied dose vector could be called the "solution" to the treatment planning problem. The latter can be calculated from the former using the equation. Moreover, it is to be noted that if rows of vbmat have been combined, split, removed, weighted or a combination of those, then the applied dose vector in step 355 should typically be calculated multiplying the original unmodified vbmat times the vector-of-beamlet-weights.

At step 360, determine whether the radiation treatment planning problem solution (applied dose vector derived from beamlet weights) is acceptable, based on criteria. If so, then the method proceeds to step 370. Otherwise, the method proceeds to step 365. The criteria on which the determination (of whether the solution is acceptable) is based can include, but is not limited to, a comparison of resulting DVH curves to desired DVH curves, and so forth. A DVH curve can be derived for each structure of interest using the applied dose vector elements corresponding to the voxels in the structure.

At step 365, identify any shortcomings in the radiation treatment planning problem solution that resulted in the solution not being determined as acceptable. The method then returns to step 310 to repeat the flow with at least one of: updated rows (per any of steps 315, 320, and 325), updated weights on the rows (per step 330), updated weights on the elements of the target vector (per any of steps 335 and 340) and updated regression process parameters (per step 345). In an embodiment, any identified shortcomings are exploited upon repeating any steps (e.g., 310, 315, 320, 325, 330, 335, 340 and/or 345) implicated by the shortcomings.

At step 370, perform a radiation therapy procedure on a patient using the integrated treatment dose information (e.g., using beamlet on-time durations at a given current derived from the regression coefficients). In an embodiment, system 200 of FIG. 2 performs the radiation therapy procedure of step 365 of method 300 of FIG. 3. Of course, other types of radiation therapy/radiation emitting systems can also be used in accordance with the teachings of the present principles while maintaining the spirit of the present principles.

Additionally regarding step 345, the regression can be an L1-penalized regression. An L1-penalized regression (also referred to as Least Absolute Shrinkage and Selection Operator (LASSO) regression) solves the regression problem, finding the set of regression coefficients (i.e., the vector-of-beamlet-weights) that minimizes a sum of two terms. The first term is a constant times the error function of the residuals between the resulting dose vector and the target vector, e.g., sum of squares of the residuals. The second term is a weighting factor multiplied the sum of the absolute values of the regression coefficients. In an embodiment, a non-negativity constraint is used as well. Since in an embodiment, the beamlet weights are set equal to the regression coefficients, the non-negativity constraint constrains the beamlets weights to non-negative values. The LASSO regression can be done using, for example, the R function penalized with the L1 tuning factor set to a non-zero positive number, the L2 tuning factor set to zero, specification of no intercept term, model set to linear, no standardizing of covariates, specification of all beamlets subject to being penalized and the non-negative coefficient constraint parameter set to true. The LASSO regression favors solutions that set beamlet weights to zero. Zero beamlet weight means the beamlet is not applied in the solution. Since it takes time during treatment to change beamlet settings, e.g., angle, energy and scan matrix location, it is desirable to set beamlet durations to zero to shorten treatment time. Different penalty function parameters, e.g., tuning parameters, can be used on repeats of Step 345. Tuning parameters can be used to trade-off reducing the number of non-zero coefficients against other objectives. Small non-zero regression coefficients (beamlet weights) can be set to zero to keep treatment time short, potentially at a small impact to solution quality.

Also regarding step 345, the regression can be a "Group LASSO" regression. A Group LASSO regression solves the regression problem, finding the set of regression coefficients (i.e., the vector-of-beamlet-weights) that minimizes a sum of terms where the first term is a constant times the square of the L2-norm of a difference, where the difference is the target vector minus a sum over non-overlapping groups of beamlets of a product, where the product is the subset of vbmat columns corresponding to the beamlets in the group multiplied by the vector of regression coefficients corresponding to the beamlets in the group. The second term is a weighting factor times a sum over non-overlapping groups of beamlets of a function of the regression coefficients corresponding to the beamlets in the group. The function of the regression coefficients corresponding to the beamlets in the group is a multiplier that accounts for the number of regression coefficients in the group, e.g., the square root of the number of regression coefficients in the group, multiplied by the L2-norm of the regression coefficients in the group. The L2-norm is the square root of the sum of squares of the regression coefficients. In an embodiment, a non-negativity constraint is used as well. The Group LASSO can be a "Standardized Group LASSO," in which case the function (in the second term) of the regression coefficients corresponding to beamlets in the group is a multiplier that accounts for the number of regression coefficients in the group, e.g., the square root of the number of regression coefficients in the group, multiplied by the L2-norm of a product, where the product is the subset of vbmat columns corresponding to the beamlets in the group multiplied by the vector of the regression coefficients corresponding to beamlets in the group. In an embodiment, a non-negativity constraint is used as well. The Group LASSO can also be a "Sparse Group LASSO" that adds to the objective to be minimized in the Group LASSO a weight multiplied by a third term, where the third term is the sum of the absolute values of the regression coefficients (not summed over non-overlapping groups). In an embodiment, a non-negativity constraint is used as well. Small non-zero regression coefficients (beamlet weights) can be set to zero to keep treatment time short, potentially at a small impact to solution quality.

Since it takes time and is therefore expensive to change machine angles, it is desirable to minimize the number of unique angles in a treatment planning solution. Setting as groups beamlets corresponding to the same angle allows Group LASSO regression to produce solutions biased toward producing non-zero coefficients for some angles, but zero coefficients for other angles, requiring fewer unique angles during treatment. Typically during therapy an angle is set and then beams of various energies are applied. Since it takes time to change energies, it is also desirable to minimize the number of energies applied at each angle. Setting as groups beamlets corresponding to the same angle-energy combination facilitates a Group LASSO solution that is biased toward producing non-zero coefficients for some angle-energy combinations, but zero coefficients for other angle-energy combinations, leading to decreased treatment time. In an embodiment, a non-negativity constraint is used as well. Other forms of penalized regression can be used as well. In an embodiment, different penalty functions or penalty function parameters, e.g., tuning parameters, can be used on repeats of Step 345. Tuning parameters can be used to trade-off reducing the number of groups with non-zero coefficients against other objectives. Small non-zero regression coefficients (beamlet weights) can be set to zero to keep treatment time short, potentially at a small impact to solution quality.

These and other variations and optimizations to the steps of method 300 are readily determined by one of ordinary skill in the art given the teachings of the present principles provided herein, while maintaining the spirit of the present principles.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method, comprising:
   splitting, by a processor based on radiation beamlet contributions to neighboring voxels, at least one row in a voxel-beamlet matrix and corresponding elements of a target dose vector prior to, and in preparation for, a regression operation, the voxel-beamlet matrix having a row for each of a plurality of voxels in a three-dimensional patient volume and a column for each of a plurality of radiation beamlets, the target dose vector representing a desired energy amount for each of the plurality of voxels in the three-dimensional patient volume, the target dose vector corresponding voxel-by-voxel to rows in the voxel-beamlet matrix;
   performing, by the processor, the regression operation on the voxel-beamlet matrix and target dose vector to obtain beamlet weights; and
   determining an actual radiation dosing scheme for a given patient based on the beamlet weights.

2. The method of claim 1, further comprising combining, by the processor, two or more of the rows in the voxel-beamlet matrix and corresponding target vector elements prior to, and in preparation for, the regression operation, wherein the combining is based on at least one of (1) a spatial relationship between the two or more of the rows, and (2) one or more mathematical correlations between the two or more of the rows, the one or more mathematical correlations being independent of the spatial relationship.

3. The method of claim 1, wherein said splitting step comprises splitting at least one voxel in the at least one of the rows into multiple sub-voxels, wherein respective doses of the multiple sub-voxels are proportional to respective doses determined for at least some of the neighboring voxels with respect to the at least one voxel.

4. The method of claim 3, wherein the multiple sub-voxels have a pyramid shape.

5. The method of claim 1, wherein the method is iterative, and wherein the at least one voxel is split based on results of a prior iteration.

6. The method of claim 1, wherein the at least one voxel is split based on a geometry of the neighboring voxels with respect to the at least one voxel.

7. The method of claim 1, wherein at least one of the at least one voxel is split into at least two sub-voxels, and the method further comprising removing one of the at least two sub-voxels from the voxel-beamlet matrix.

8. The method of claim 1, wherein the at least one voxel is split based on a residual of the at least one voxel.

9. The method of claim 1, wherein the method is iterative, and said splitting step splits at least one different voxel in a particular iteration compared to another iteration.

10. The method of claim 1, further comprising removing, by the processor, at least one of the rows from the voxel-beamlet matrix and corresponding target vector elements prior to, and in preparation for, the regression operation, wherein the removing is based on a prior radiation treatment planning solution showing a dose in an Organ At Risk corresponding to the at least one of the rows that is above an Organ At Risk dose threshold.

11. The method of claim 1, further comprising setting, by the processor, target weights for a subset of voxels corresponding to a given structure based on a confidence value, the confidence value depending on a number of simulated particles such that the target weights increase with decreasing confidence value for target volume voxels and decrease with decreasing confidence value for Organ At Risk voxels.

12. The method of claim 1, further comprising performing, by a radiation therapy machine, the radiation therapy procedure on the patient using the beamlet on-time durations and currents derived from the beamlet weights.

13. The method of claim 1, further comprising reducing a total number of non-zero coefficients from among output regression coefficients of the regression process by applying a penalty on the output regression coefficients using a Least Absolute Shrinkage and Selection Operator.

14. The method of claim 1, wherein a Group Least Absolute Shrinkage and Selection Operator is used that comprises grouping together any of the plurality of beamlets corresponding to respective same ones of a plurality of angles to target non-zero coefficients for some of the plurality of angles and zero coefficients for other ones of the plurality of angles while targeting a reduction in a number of unique angles implicated by a given treatment planning solution from among the plurality of angles.

15. The method of claim 1, wherein a Group Least Absolute Shrinkage and Selection Operator is used that comprises grouping together any of the plurality of beamlets corresponding to a respective same energy amount at a given angle from among a plurality of possible energy amounts at the given angle to target non-zero coefficients for some of the plurality of energy amounts at the given angle and zero coefficients for other ones of the plurality of energy amounts at the given angle while targeting a reduction in a number of energy amounts implicated by a given treatment planning solution from among the plurality of possible energy amounts at the given angle.

16. A non-transitory article of manufacture tangibly embodying a computer readable program which when executed causes a computer to perform the steps of claim 1.

17. A system, comprising:
a processor, configured to:
split, based on radiation beamlet contributions to neighboring voxels, at least one row in a voxel-beamlet matrix and corresponding elements of a target dose vector prior to, and in preparation for, a regression operation, the voxel-beamlet matrix having a row for each of a plurality of voxels in a three-dimensional patient volume and a column for each of a plurality of radiation beamlets, the target dose vector representing a desired energy amount for each of the plurality of voxels in the three-dimensional patient volume, the target dose vector corresponding voxel-by-voxel to rows in the voxel-beamlet matrix;
perform the regression process on the voxel-beamlet matrix and target dose vector to obtain beamlet weights; and
determine an actual radiation dosing scheme for a given patient based on the beamlet weights.

18. The system of claim 17, further comprising reducing a total number of non-zero coefficients from among output coefficients of the regression process by applying a penalty on the output regression coefficients using a Least Absolute Shrinkage and Selection Operator.

19. The system of claim 17, wherein a Group Least Absolute Shrinkage and Selection Operator is used that comprises grouping together any of the plurality of beamlets corresponding to respective same ones of a plurality of angles to target non-zero coefficients for some of the plurality of angles and zero coefficients for other ones of the plurality of angles while targeting a reduction in a number of unique angles implicated by a given treatment planning solution from among the plurality of angles.

20. The system of claim 17, wherein a Group Least Absolute Shrinkage and Selection Operator is used that comprises grouping together any of the plurality of beamlets corresponding to a respective same energy amount at a given angle from among a plurality of possible energy amounts at the given angle to target non-zero coefficients for some of the plurality of energy amounts and zero coefficients for other ones of the plurality of energy amounts at the given angle while targeting a reduction in a number of energy amounts implicated by a given treatment planning solution from among the plurality of possible energy amounts at the given angle.

* * * * *